and al.|

United States Patent [19]

Fickenscher et al.

[11] Patent Number: 5,599,909
[45] Date of Patent: Feb. 4, 1997

[54] PROCESS FOR REACTIVATING PURIFIED MEMBRANE PROTEINS

[75] Inventors: Karl Fickenscher; Norbert F. Zander, both of Marburg, Germany

[73] Assignee: Behringwerke Aktiengesellschaft, Marburg, Germany

[21] Appl. No.: 170,880

[22] Filed: Dec. 21, 1993

[30] Foreign Application Priority Data

Dec. 23, 1992 [DE] Germany .......................... 42 43 729.6

[51] Int. Cl.⁶ .............................. C07K 1/00; C07K 14/00
[52] U.S. Cl. ...................... 530/402; 530/412; 530/413; 530/381
[58] Field of Search ..................... 530/412, 413, 530/381, 402

[56] References Cited

U.S. PATENT DOCUMENTS 5,149,529  10/1991  Ho et al. .

FOREIGN PATENT DOCUMENTS

0355845A2  2/1990  European Pat. Off. .
0433225A1  6/1991  European Pat. Off. .
WO92/08479  5/1992  WIPO .

OTHER PUBLICATIONS

"Binding of the Protein Component of Tissue Factor to Phospholipids", Pitlick et al., Biochemistry 9(26):5105–5113 (1970).

"Cloning And Expression Of Human Tissue Factor cDNA", Fisher et al., Thrombosis Research 48:89–99 (1987).

"Molecular Cloning of the cDNA for Tissue Factor, the Cellular Receptor for the Initiation of the Coagulation Protease Cascade", Morrissey et al., Cell 50:129–135 (1987).

"Purification of Human Brain Tissue Factor", Broze, Jr., et al., The Journal of Biological Chemistry 260(20):10917–10920 (1985).

"Purification and Characterization of Bovine Tissue Factor", Bach et al., The Journal of Biological Chemistry 256(16):8324–8331 (1981).

"Reconstitution And Lipid Requirements Of Porcine Tissue Thromboplastin", Wijngaards et al., Biochimica et Biophysica Acta 488:161–171 (1977).

Darnell et al., "Molecular Cell Biology", 1986, pp. 59–60, 569–583.

Cantor et al., "Biophysical Chemistry", pp. 287–288.

Derwent Publications Abstract J02188532.

*Primary Examiner*—Christina Y. Chan
*Assistant Examiner*—Frank C. Eisenschenk
*Attorney, Agent, or Firm*—Finnegan, Henderson, Farabow, Garrett & Dunner, L.L.P.

[57] ABSTRACT

Processes for reactivating membrane proteins are disclosed. The membrane proteins are reactivated by mixing membrane proteins with phospholipids, in the absence of detergents, at acidic pH, followed by neutralization by buffer addition, or by mixing membrane proteins with phospholipids, in the absence of detergents, at elevated temperature, followed by buffer addition

10 Claims, 5 Drawing Sheets

PROCESS FOR REACTIVATING PURIFIED MEMBRANE PROTEINS

The invention relates to a process for reactivating purified membrane proteins.

Membrane proteins (e.g. receptors) are composed of one or more transmembrane domains together with intracellular and extracellular domains. The activity of such proteins is frequently measured following integration of the purified protein into an artificial membrane.

Tissue factor (tissue thromboplastin) can serve as an example. This receptor for factor VII of the blood coagulation system is composed of apoprotein and lipids (Pitlick, F. A. and Nemerson, Y., 1970). The apoprotein is a glycosylated polypeptide of 263 amino acids. Close to the carboxy-terminal end, it possesses a hydrophobic sequence of 23 amino acids by which it is anchored in the membrane. The intracellular moiety is composed of 21 amino acids (Fisher et al., 1987; Morrissey et at., 1987). In vivo, tissue factor is present as an integral membrane protein of cells which are not in direct contact with the blood. Its physiological function as a cell-surface receptor comprises binding and activating plasma coagulation factor VII upon coming into contact with blood or plasma. This complex possesses serine protease activity and is able to activate factors IX and X and thereby trigger coagulation.

There are two different methods for isolating tissue factor. In one of these, the active tissue factor is partially purified by disrupting suitable tissue and isolating the membrane fraction. This material is primarily used for preparing diagnostic reagents for examining blood coagulation in plasma. Since the membrane protein is isolated including bound lipid molecules no reactivation of the apoprotein is necessary.

In the second process, the isolated apoprotein is obtained. Since it has lost most of its activity (Broze, G. J. et al., 1985), it has to be reactivated. For this purpose it has to be integrated once more into a lipid membrane (Pitlick, F. A. and Nemerson, Y., 1970; Bach et al., 1981). This process is essential for protein obtained by the recombinant route, since the microbiological organisms producing it are not able to provide a sufficiently active membrane protein. These considerations in principle also apply to proteins which can be prepared by partial or total synthesis in vitro.

A number of processes are known for reincorporating purified membrane proteins into a lipid membrane. For this purpose, an aqueous suspension of phospholipids is normally prepared using a detergent. e.g. deoxycholate. This suspension is mixed with the purified membrane protein. Subsequently, the detergent is removed, for example using dialysis. By mixing apoprotein with the phospholipid suspension, or by removing the detergent the protein is incorporated into forming membrane vesicles (Pitlick, F. A. and Nemerson, Y., 1970). Deoxycholate is the preferred detergent, since it can be removed by dialysis. However, in principle, other detergents can also be employed if they can be removed from the mixture.

Thus, Wijngaards et al. described a process for relipidizing tissue factor using sodium taurocholate as Me detergent. They found a pH optimum at pH 4.0, but had to remove the detergent from the mixture after relipidization.

A fundamental disadvantage in using detergents is the need to remove these auxiliary agents from the mixture. Although they mediate the incorporation of protein into a membrane, they strongly interfere with the activity of the membrane-protein complex, since they are also integrated into the lipid vesicles. In order to remove the detergent, the mixture is as a rule dialyzed against a large volume of buffer. This step is time-consuming and laborious, and leads to losses in yield and activity. In addition, it is not possible to remove the detergents completely in this manner.

The invention was based on the object of making available a simple process of reactivating purified membrane proteins without using detergents, such that they correspond functionally to proteins in a physiological environment. This reactivation comprises incorporating the relevant membrane protein into suitable lipid micelles (relipidization). This is the only manner in which the natural physiological activity of purified tissue factor apoprotein in the coagulation process can be restored.

It has been found, surprisingly, that relipidization can be achieved without the aid of detergents, by acidifying and/or heating a protein/lipid mixture.

In principle, the process according to the invention can also be applied to mixtures of purified proteins.

It has been found that the relipidization can be achieved by mixing protein and phospholipids at sufficiently low pH values. In this process, the phospholipids do not need to be dissolved with the aid of a detergent, but, instead, it is sufficient to emulsify them in an aqueous solution. The pH can be adjusted once again to the desired value immediately after mixing the sample to achieve homogeneity. Appropriate pH ranges are between pH 1 and 5, preferably between pH 2 to 4, particularly preferably at a pH of about 3. Natural phospholipid mixtures of plant or animal origin known by a person skilled in the art can be used. Defined pure substances or mixtures thereof, which are known to the person skilled in the art, can likewise be employed. Preferably, the process according to the invention is carried out using mixtures of vegetable phospholipids.

The relipidization can be carried out using a membrane protein which is dissolved or one which is bound to an affinity column (e.g. an immuno-adsorption column containing a polyclonal or monoclonal antibody). In principle, a membrane protein of human, plant, animal, microbial or recombinant origin can be used; it is likewise possible to use a mutant of a naturally occurring protein. The use of a dissolved membrane protein in a concentration of up to 50 mg/ml is preferred. In this case, an aqueous emulsion of phospholipids of up to 200 mg/ml, preferably up to 50 mg/ml is initially mixed with buffer at acid pH. Purified membrane protein is subsequently added to this acidic emulsion, and mixed. After an incubation time betwen 1 and 10 min, preferably between 2 and 6 min, the mixture is neutralized by adding buffer.

The objective of the invention can also be achieved in a second embodiment for integrating membrane proteins into a lipid membrane, by heating a protein in the presence of phospholipids. As in the process involving acidification it is not necessary to dissolve the lipids with the aid of detergents. The materials which have already been mentioned above can be used as the phospholipids.

Type and preferred concentration range of membrane protein and phospholipid employed are the same as in the first embodiment of the invention.

Heating may be carried out at a temperature between 50° C. and 130° C. Heating at 80° C. to 95° C. for 1 to 10 min is preferred, preferably for about 4 to 6 min. Subsequently, the mixture is cooled to room temperature within between 1 and 10 min, preferably for about 4 to 6 min, and buffer is subsequently added.

Following relipidization, the membrane protein is present in active form incorporated into a lipid membrane. It can be provided with suitable additives and be subjected to further processing. If tissue factor apoprotein is relipidized using one of the processes according to the invention, its use as a therapeutic. agent or diagnostic agent becomes possible. In the second case, the relipidized tissue factor can be processed, in particular, to produce a reagent for determining the prothrombin time for the purposes of examining blood coagulation in plasma.

It is intended to illustrate the invention in more detail below, using the example of tissue factor apoprotein. Thus the present invention relates to a detergent-free, reactivated tissue factor apoprotein, which is obtained by a process for reactivating purified membrane proteins, wherein the reaction of the membrane proteins with phospholipids is effected without detergents. The present invention also relates to a reagent for determining prothrombin time, said reagent containing a detergent-free reactivated tissue factor apoprotein obtained by the present process. The invention further relates to a pharmaceutical composition containing tissue factor apoprotein obtained by the process of the present invention and a pharmaceutically acceptable excipient.

EXAMPLE 1

Relipidization of a recombinant and purified human thromboplastin apoprotein by acidification Human tissue factor apoprotein was expressed in *E. coli*. The protein was purified from the *E. coli* extract using an immunoabsorption column and diluted to 10 μg/ml.

The following reagents were combined for the relipidization mixture:

50 μl of phospholipid suspension (0.5% w/v Phospholipon 25 P, in distilled water, from Nattermann, Germany)

50 μl of 0.1M glycine, adjusted with HCl to pH 2.5

After mixing, the sample was incubated at room temperature for 5 min and then

100 μl of tissue factor apoprotein were added. After mixing again, the sample was incubated at room temperature for 1 min and 800 μl of 50 mM N-2-hydroxyethhylpiperazine-N'-2-ethanesulfonic acid, 5 g/l glycine, 13 mM $CaCl_2$, 0.1% $NAN_3$, pH 7.5 were then added.

The prothrombin time was determined in a Schnitger and Gross coagulometer (0.1 ml of normal human plasma pool +0.2 ml of relipidized tissue factor), giving a coagulation time of 11.0 s.

EXAMPLE 2 pH-dependency of the relipidization

Relipidization of the tissue factor was performed as described in Example 1. However, glycine buffers of different pH values (pH 1.5 to 13.5) were employed. The pH was measured after mixing the, Phospholipon suspension with the tissue. factor. FIG. 1 depicts the relationship between the measured pH in the relipidization mixture and the prothrombin time obtained. A pH optimum of between pH 3 and pH 5 results. Within this range, the measured prothrombin times are comparable with prothrombin times measured with the same quantity of native tissue factor isolated from tissue. It was not possible to achieve lower pH values in the relipidization mixture with the selected buffer, but such pH values would also be expected to be suitable.

EXAMPLE 3

Time-dependency of the relipidization by acidification

Relipidization was performed as described in Example 1. The mixtures were neutralized at various time intervals between 10 s and 10 min after mixing lipid and protein. Subsequently, the prothrombin time of a normal human plasma pool was determined by coagulometry. FIG. 2 shows the relationship between the duration of incubation at acid pH and the measured prothrombin times. The prothrombin time is only slightly dependent on the, duration of incubation at acid pH; the shortest prothrombin time is obtained with a duration of incubation between 5 and 10 min.

EXAMPLE 4

Relipidization by heating

The following reagents were combined to form a relipidization mixture:

100 μl of tissue factor apoprotein (10 μg/ml)

100 μl of 0.5% (w/v) Phospholipon 25 P in distilled water.

The mixture was exposed to a temperature of between 25° C. and 95° C. for 5 min. Subsequently, it was cooled down to room temperature within 5 minutes and 800 μl of 50 mM N-2-hydroxyethylpiperazine-N'-2-ethanesulfonic acid, 5 g/l glycine, 13 mM $CaCl_2$, 0.1% $NAN_3$, pH 7.5 were added. The prothrombin time of a normal human plasma pool was determined in a Schnitger and Gross coagulometer. FIG. 3 shows the relationship between the temperature in the heating step and the measured prothrombin time. The shortest time is obtained with a heating step of 95° C. Temperatures above 80° C. result in shorter prothrombin times than those which are measured with a corresponding quantity of native tissue factor. FIG. 4 shows the relationship between the duration of a heating step at 95° C. and the measured prothrombin time of a normal human plasma pool. The relipidization can be achieved using a heating step of only 1 minute in duration.

EXAMPLE 5

Quality of the reagents: sensitivity to factor VII

A normal human plasma pool was diluted with a factor VII deficient plasma (Behringwerke AG, Marburg, Germany). Factor VII concentrations between 100% and 10% (based on the normal human plasma pool) were used.

The prothrombin times of the samples were subsequently determined in a Schnitger and Groβ coagulometer. The measured times were related to the prothrombin time of the normal human plasma pool.

FIG. 5 shows the relative prothrombin times [ratio=(PT)/($PT_{100}$% factor VII)] in dependence on the factor VII concentration in the sample. Two tissue factor reagents were used:

a) A native tissue factor, isolated from human placenta (Thromborel S, Behringwerke AG)

b) A reagent prepared by a process according to the invention (as in Example 1), starting from recombinant tissue factor apoprotein.

The normal range of factor VII concentration in a human population (95 percentile) is given by prothrombin ratios of 1.00±0.20. Plasmas with a prothrombin ratio lying outside this range are considered to be pathological. The factor VII concentration corresponding to this sensitivity limit is very similar for both reagents used here.

pH-dependency of relipidization

Figure 1:
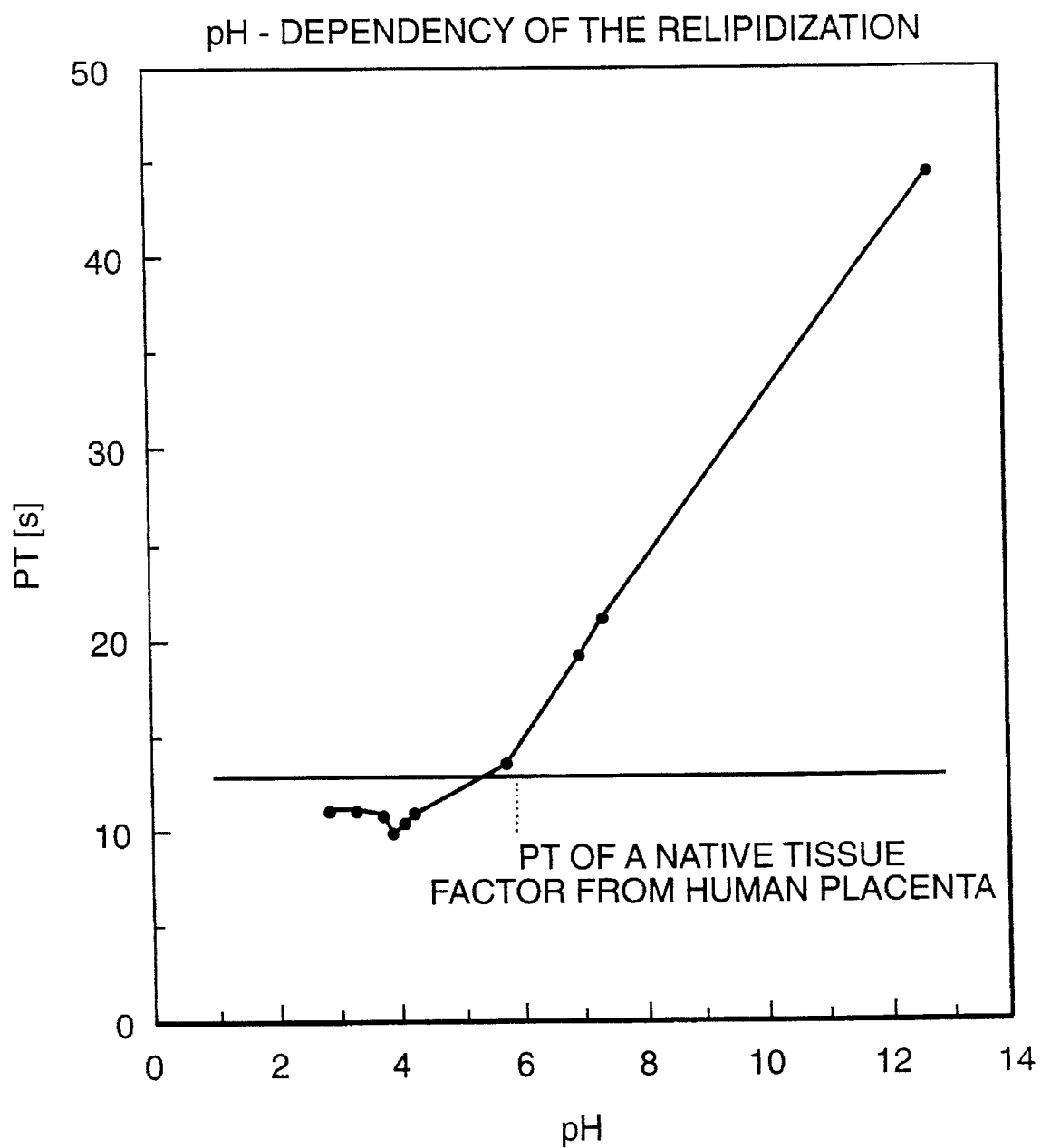
FIG. 1.
Figure 2:
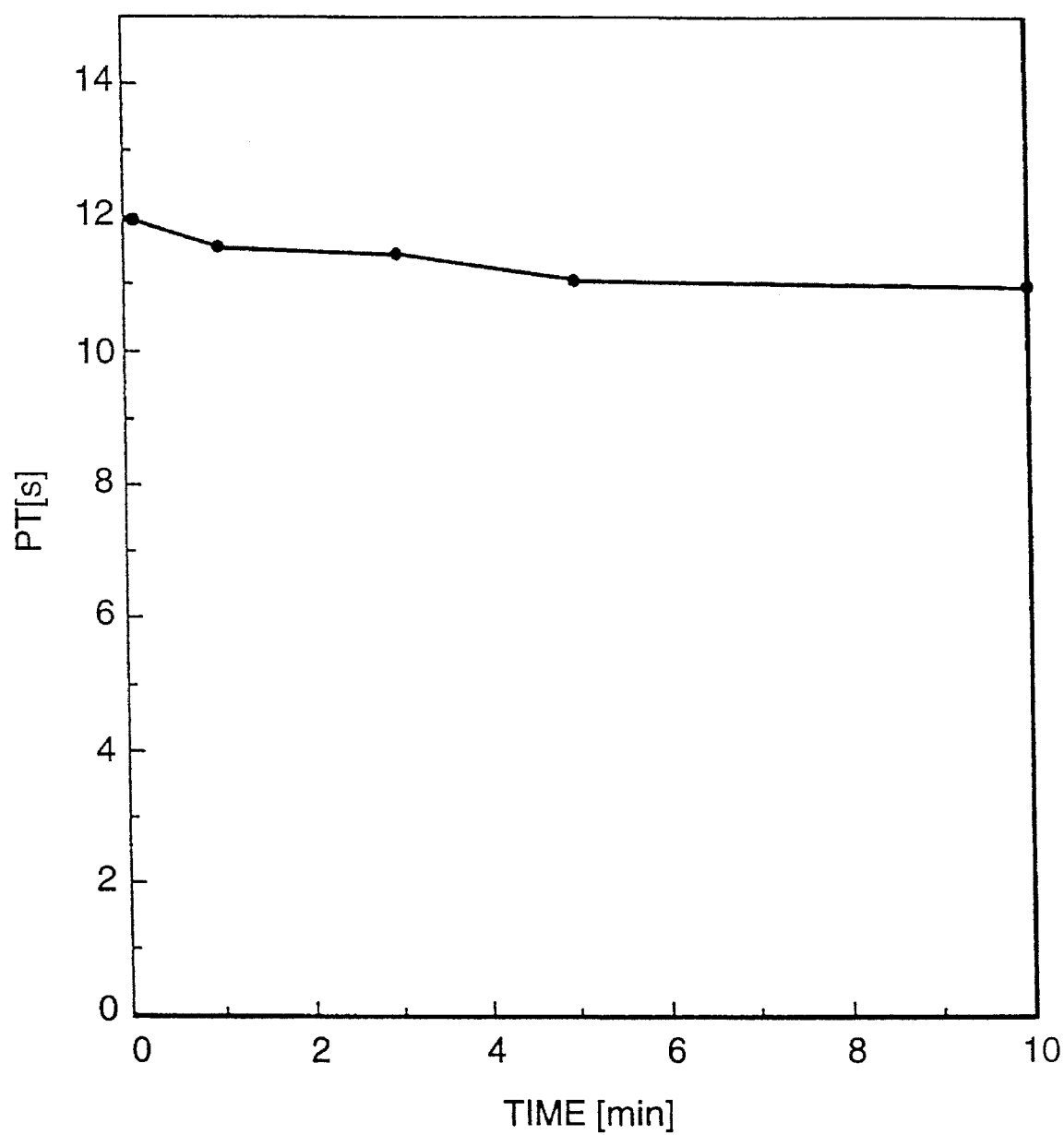
Figure 3:
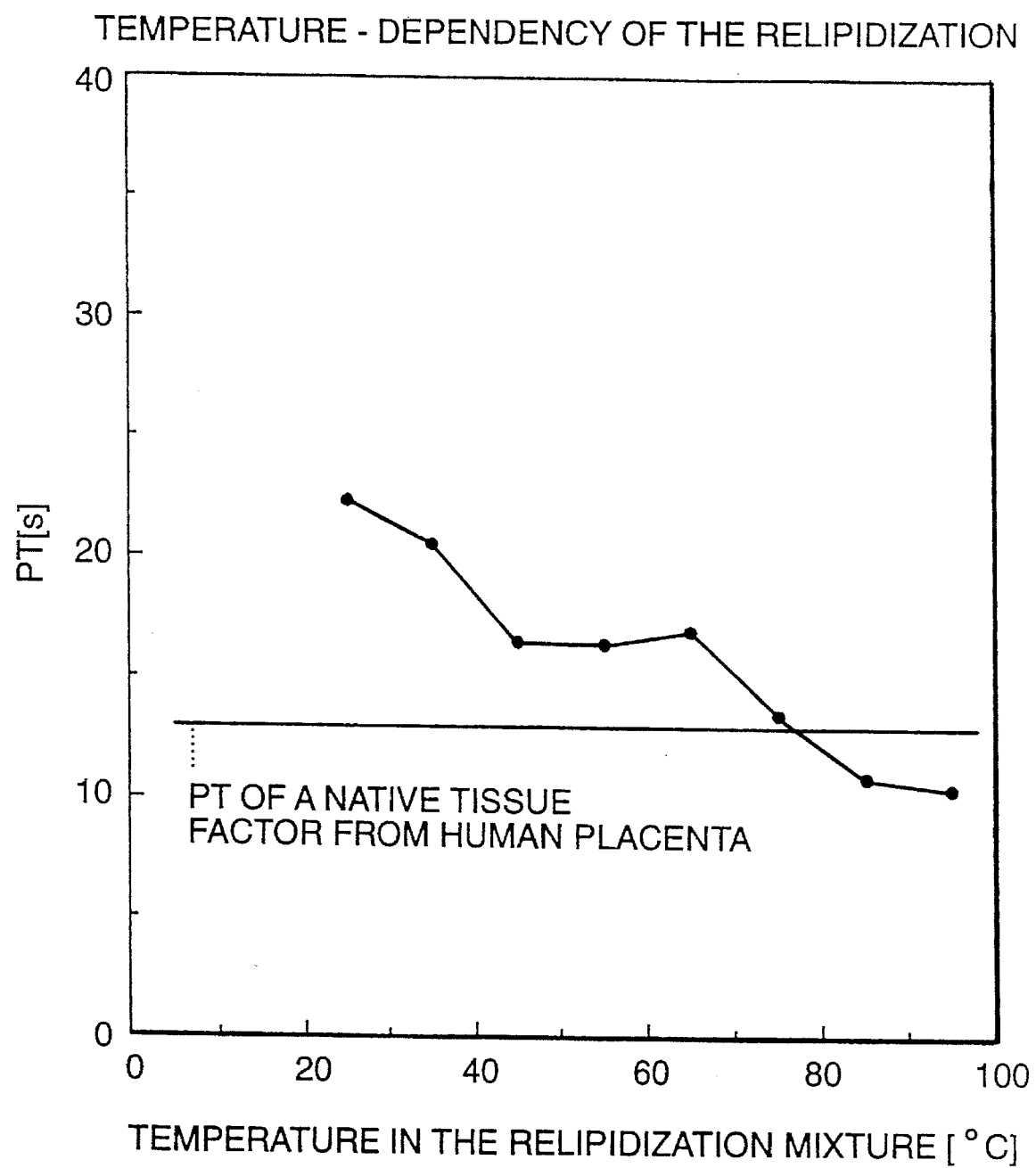
Figure 4:
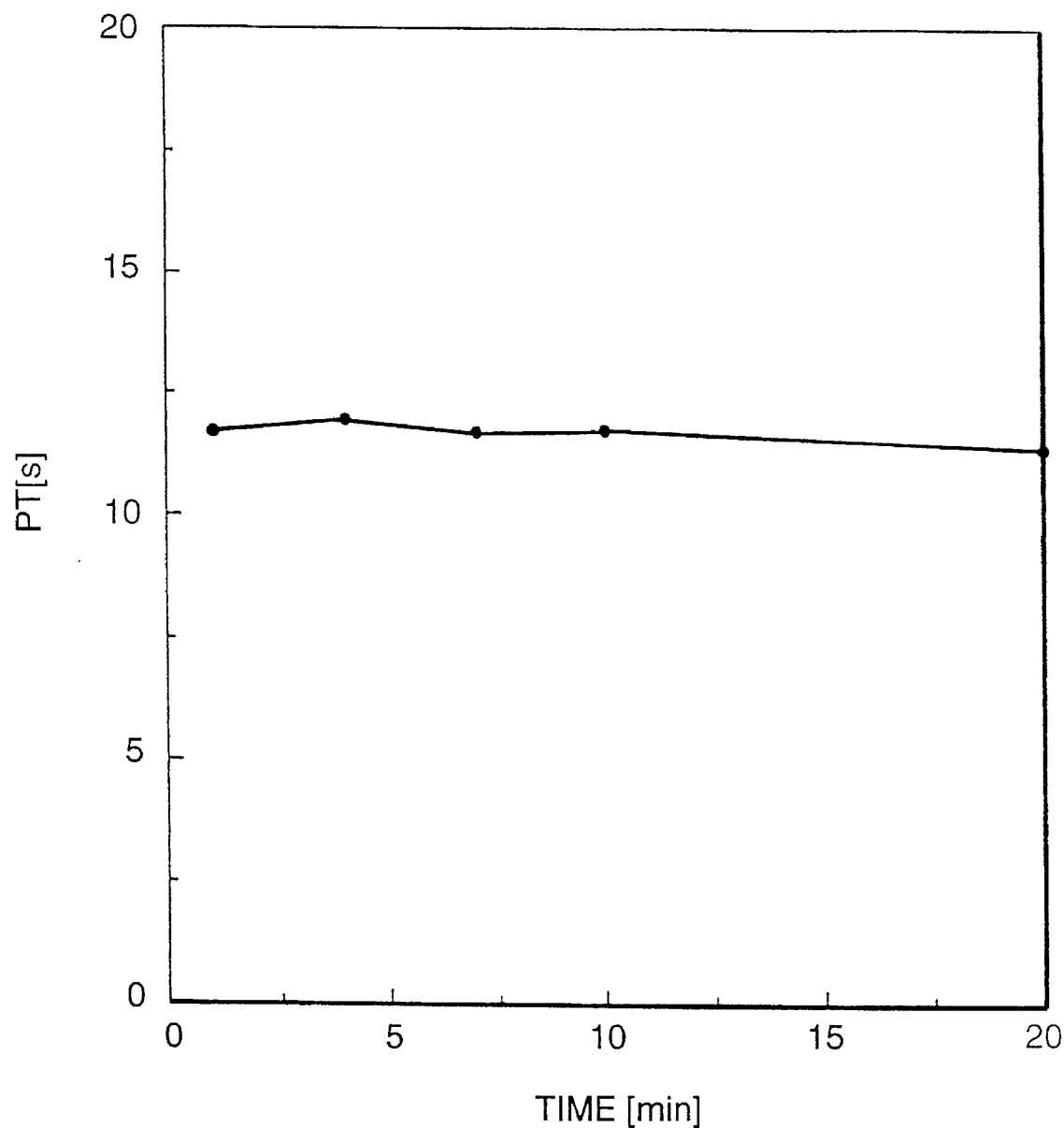
Figure 5:
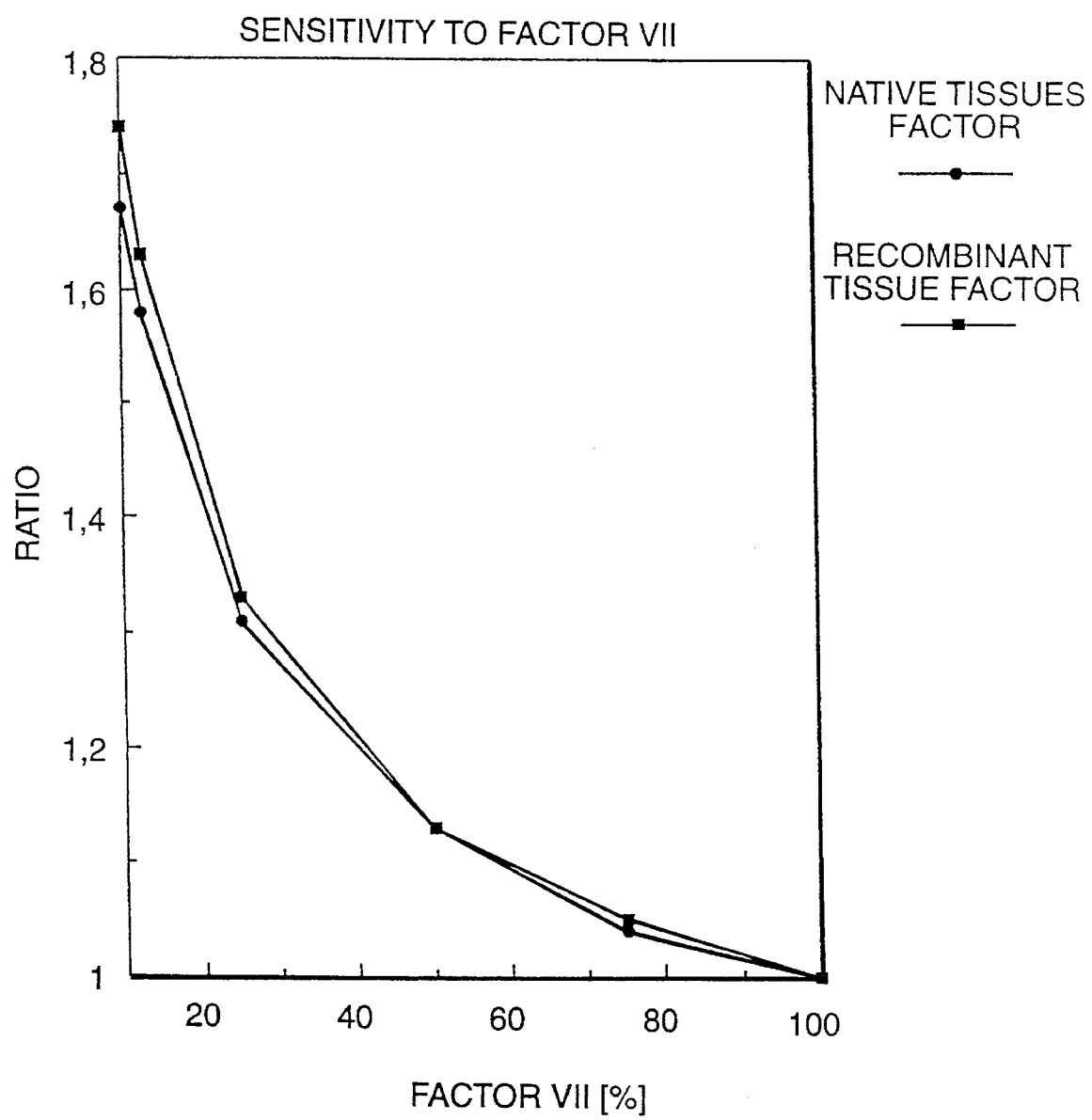

The reagents were prepared as described in Example 1 and Example 2. Phospholipon 25 P was premixed with glycine buffers of different pH values, After adding the tissue factor apoprotein, the pH was measured and the mixture was subsequently neutralized, The prothrombin time (PT) of a normal human plasma pool was determined by coagulometry in a Schnitger and Groβ coagulometer (average value of a duplicate determination).

FIG. 2:

Time-dependency of the relipidization under acid conditions

The reagents were prepared as described in Example 1 and Example 3. The figure shows the prothrombin time PT of a normal human plasma pool (average value of a duplicate determination) with varying durations of incubation at acid pH.

FIG. 3:

Dependency of the replipidization on the temperature of the heating step

The reagents were prepared as described in Example 4. This figure shows the prothrombin time of a normal human plasma pool (average value of a duplicate determination) in dependence on the temperature of a five-minute heating step.

FIG. 4:

Time-dependency of the relipidization by heating

The figure shows the prothrombin time PT of a normal human plasma pool (average value of a duplicate determination) in dependence on the length of a heat treatment at 95° C.

FIG. 5:

Sensitivity to factor VII

The reagent was prepared in accordance with Example 1, and the normal human plasma pool was diluted with factor VII deficient plasma in accordance to Example 5.

The figure shows the relative prothrombin time [ratio= $(PT)/(PT_{100}\%$ factor-VII)] in dependence on the factor VII concentration. The reagent, which was prepared from recombinant tissue factor in accordance with a process according to the invention, was compared with a native, partially purified tissue factor from human placenta. (Thromborel S, Behringwerke AG).

We claim:

1. A process for reactivating purified membrane proteins, which comprises reacting said membrane proteins with phospholipids, said process being effected without adding detergents.

2. The process as claimed in claim 1, wherein the reactivation is carried out under acidic conditions.

3. The process as claimed in claim 1, wherein the reactivation is carried out at elevated temperature.

4. The process as claimed in claim 1, wherein the reactivation is carried out under acidic conditions at elevated temperatures.

5. The process as claimed in claim 2, wherein the pH is between 1 and 5.

6. The process as claimed in claim 3, which is carried out at a temperature between 50° C. and 130° C.

7. The process as claimed in claim 1, which is carried out using pure phospholipids of plant or animal origin, defined mixtures of pure phospholipids, or natural lipid mixtures.

8. The process as claimed in claim 1, which is carried out using membrane proteins dissolved in aqueous solution.

9. A process as claimed in claim 5, which is carried out for between 1 and 10 minutes.

10. A process as claimed in claim 3, which is carried out at a temperature between 50° C. and 130° C. for between 1 and 10 minutes, followed by cooling the mixture to room temperature within between 1 and 10 minutes, and adding a buffer.

* * * * *